(12) United States Patent
Tang et al.

(10) Patent No.: US 10,568,360 B2
(45) Date of Patent: *Feb. 25, 2020

(54) PRESS PUFFING DEVICE

(71) Applicant: CHINA TOBACCO YUNNAN INDUSTRIAL CO., LTD, Kunming (CN)

(72) Inventors: Jianguo Tang, Kunming (CN); Xudong Zheng, Kunming (CN); Xu Zeng, Kunming (CN); Ru Wang, Kunming (CN); Chengya Wang, Kunming (CN); Weimin Gong, Kunming (CN); Zhiqiang Li, Kunming (CN); Ping Lei, Kunming (CN); Shanzhai Shang, Kunming (CN); Jingmei Han, Kunming (CN); Dalin Yuan, Kunming (CN); Shunliang Tang, Kunming (CN); Yongkuan Chen, Kunming (CN); Hongyong Luo, Kunming (CN)

(73) Assignee: CHINA TOBACCO YUNNAN INDUSTRIAL CO., LTD, Kunming (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/326,927

(22) PCT Filed: Aug. 29, 2017

(86) PCT No.: PCT/CN2017/099527
§ 371 (c)(1),
(2) Date: Feb. 21, 2019

(87) PCT Pub. No.: WO2018/041105
PCT Pub. Date: Mar. 8, 2018

(65) Prior Publication Data
US 2019/0223505 A1 Jul. 25, 2019

(30) Foreign Application Priority Data

Aug. 31, 2016 (CN) .......................... 2016 1 0791004

(51) Int. Cl.
*A24F 47/00* (2006.01)
*F04B 35/04* (2006.01)
(Continued)

(52) U.S. Cl.
CPC ............ *A24F 47/008* (2013.01); *A24F 47/00* (2013.01); *F04B 35/04* (2013.01); *F04B 37/10* (2013.01); *H05B 3/46* (2013.01)

(58) Field of Classification Search
CPC ....................................................... A24F 47/008
See application file for complete search history.

(56) References Cited

U.S. PATENT DOCUMENTS

2009/0133691 A1* 5/2009 Yamada ............... A61M 11/041
128/200.16
2009/0183744 A1* 7/2009 Hayton ................ A61M 11/007
131/270

(Continued)

FOREIGN PATENT DOCUMENTS

| CN | 2211171 Y | 1/1995 |
|---|---|---|
| CN | 1397381 A | 2/2003 |

(Continued)

*Primary Examiner* — Michael J Felton
*Assistant Examiner* — Sonny V Nguyen
(74) *Attorney, Agent, or Firm* — Bayramoglu Law Offices LLC (57) ABSTRACT

A press puffing device includes a piston support, a nozzle holder, and a sealing fixer. In the press puffing device, a power supply start button is pressed to produce an aroma gas, and the aroma gas is contained in the cylindrical inner (Continued)

cavity. By pressing the piston support, the contained smoke is compressed and flows to the air outlet through the lateral gas channel to spurt out.

4 Claims, 6 Drawing Sheets

(51) Int. Cl.
*F04B 37/10* (2006.01)
*H05B 3/46* (2006.01)

(56) References Cited

U.S. PATENT DOCUMENTS

| | | | |
|---|---|---|---|
| 2013/0220316 A1* | 8/2013 | Oglesby | A24F 47/006 128/202.21 |
| 2014/0217085 A1* | 8/2014 | Alima | A24F 47/008 219/474 |
| 2015/0027470 A1* | 1/2015 | Kane | A24F 47/008 131/329 |
| 2015/0150305 A1* | 6/2015 | Shenkal | A24F 47/008 131/329 |
| 2017/0215474 A1* | 8/2017 | Li | A24F 47/008 |
| 2017/0258140 A1* | 9/2017 | Rostami | A24F 47/008 |
| 2017/0265526 A1* | 9/2017 | Li | B05B 7/0012 |
| 2017/0280772 A1* | 10/2017 | Batista | A24F 47/008 |
| 2019/0208811 A1* | 7/2019 | Biel | A24F 15/18 |
| 2019/0274358 A1* | 9/2019 | Reevell | A24F 7/00 |

FOREIGN PATENT DOCUMENTS

| | | |
|---|---|---|
| CN | 1880853 A | 12/2006 |
| CN | 201067713 Y | 6/2008 |
| CN | 103859607 A | 6/2014 |
| CN | 106263038 A | 1/2017 |
| CN | 106263039 A | 1/2017 |
| CN | 206025227 U | 3/2017 |
| CN | 206586391 U | 10/2017 |
| GB | 2285396 A | 7/1995 |

* cited by examiner

PRESS PUFFING DEVICE

CROSS REFERENCE TO RELATED APPLICATIONS

This application is the national phase entry of international Application No. PCT/CN2017/099527, filed on Aug. 29, 2017, which is based upon and claims priority to Chinese Patent Application No. 201610791004.5, filed on Aug. 31, 2016, the entire contents of which are incorporated herein by reference.

TECHNICAL FIELD

The present invention belongs to the field of cigarettes and electronic cigarettes, and in particular, relates to a press and snorting type smoking paraphernalia for heating cigarettes, and further to a press puffing device.

BACKGROUND

The drip tip of the existing smoking paraphernalia for cigarette is generally made of plastic or metal, and a layer of chemical substance is electroplated or sprayed on the surface of the plastic or metal material to form a solidified protective layer (such as a metal plating layer, a paint coating layer). The smoking paraphernalia may be subjected to a pyrolysis at a certain temperature to generate harmful substances that affect human health. In some occasions, the smoke generated by the smoking paraphernalia is banned; the common smoking paraphernalia for cigarette is designed with airflow channels from the air inlet to the heating chamber and then to the air outlet. The conductive heating method is used in the heating chamber of the common smoking paraphernalia for cigarette; namely, the heating element is in direct contact with the cigarette, and the heat generated by the heating element is directly transmitted to the cigarette.

One of the disadvantages of the prior art lies in the smoking mode. People smoke through the mouth by directly contacting the cigarette filter, and the material on the surface of the cigarette filter may be subjected to a pyrolysis at a certain temperature to produce harmful substances that will get inhaled. Therefore, it is desirable avoid the direct contact with the cigarette filter while smoking.

Another disadvantage of the prior art lies in the heating mode. The conductive heating method is used in the heating chamber of the common smoking paraphernalia for the cigarette, namely, a heating element (such as a metal heating wire) and a high temperature resistant material (such as ceramic) are sintered at a high temperature to form a cigarette heating tube, which transfers the heat directly to the surface of the cigarette. When the tightness between the inner wall of the heating chamber and the cigarette is not uniform, it is prone to generate over heating at the position where the inner wall of the heating chamber and the cigarette is too tight, resulting in burnt smell. Besides, another heating mode of the ordinary cigarette is designed to integrate the printing heating material and Flexible Printed Circuit (FPC) board on the outer wall of the cigarette heating tube, which makes it easy to dissipate the heat generated by the heating material through the medium material and the thermal insulation material, thereby causing heat loss.

The present invention is aimed at solving the above-mentioned problems.

SUMMARY

In view of the disadvantages of the existing cigarette smoking paraphernalia, a press and snorting type smoking paraphernalia for heating a cigarette is designed in the present invention, namely, the smoke from the smoke outlet of the press and snorting type smoking paraphernalia for the cigarette is inhaled by the nose, rather than the mouth directly contacting the cigarette filter, so as to achieve the non-contact smoking.

A first aspect of the present invention relates to a press and snorting type smoking paraphernalia for heating the cigarette, including:

A. a roasting-type heating device, including:

a cigarette heating tube 15, wherein a plurality of wall holes 151 are provided on a side wall of the cigarette heating tube;

a heating element 6, wherein the heating element is disposed on an outer side of the cigarette heating tube 15 and is not in contact with the cigarette heating tube; and a thermal insulation pipe 7, wherein the thermal insulation pipe is sleeved on the outer side of the heating element 6 and is not in contact with the heating element; and B. a press puffing device, including:

a piston support 2 including a left cylindrical cavity 21, a right cylindrical cavity 22, and a connection portion 23 between the left cylindrical cavity and the right cylindrical cavity, wherein both upper and lower ends of the left cylindrical cavity 21 and the right cylindrical cavity 22 are open;

a nozzle holder 12, including a cylindrical inner cavity 123 with a roof, wherein a bottom opening of the inner cavity 123 is connected to the cigarette heating tube 15 for air to pass through; a lateral gas channel 124 is provided on a side wall of the inner cavity 123; the lateral gas channel 124 is connected to an air outlet 121 for air to pass through; and a nozzle holder guide slot 122 penetrating the side wall of the cylindrical inner cavity 123 is provided thereon; and a sealing fixer 14 including a left cavity 141, a right cavity 142 and a partition wall 143 between the left cavity and the right cavity, wherein a sealing fixer sliding slot 144 is provided on the partition wall 143; and an inner shape of the left cavity 141 is matched with an outer shape of the nozzle holder 12;

wherein, positional relationships of various components in the press puffing device are as follows:

the nozzle holder 12 is contained in the left cavity 141 of the sealingfixer 14; the right cylindrical cavity 22 of the piston support 2 is contained in the right cavity 142; the sealing fixer sliding slot 144 and the nozzle holder guide slot 122 are configured to overlap each other; the connection portion 23 of the piston support 2 is allowed to pass through and slide upwards and downwards in the sealing fixer sliding slot 144 and the nozzle holder guide slot 122; the left cylindrical cavity 21 of the piston support 2 is contained in the cylindrical inner cavity 123 of the nozzle holder 12; a top end of the left cylindrical cavity 21 can be appressed or not appressed with the roof of the cylindrical inner cavity 123; a side wall of the left cylindrical cavity 21 closes the lateral gas channel 124 when the top end of the left cylindrical cavity 21 is appressed with the roof, and opens the lateral gas channel 124 when the top end of the left cylindrical cavity 21 is not appressed with the roof.

Preferably, a sealing ring 13 is sleeved between the left cylindrical cavity 21 of the piston support 2 and the cylindrical inner cavity 123 of the nozzle holder 12.

Preferably; a spring 3 is contained in the right cavity 142 of the sealing fixer 14; one end of the spring abuts against a lower end wall of the right cylindrical cavity 22 of the piston support 2, and other end of the spring abuts against a bottom wall of the sealing fixer 14; when a user no longer presses the piston support 2, the piston support 2 is bounced back by a reset action of the spring.

Preferably, a radial inner edge 24 is provided at a top end opening of the left cylindrical cavity 21 of the piston support 2. Such arrangement of the inner edge 24 is aimed at increasing a compression area of gas in the cylindrical inner cavity 123 when the left cylindrical cavity 21 moves downward, thereby improving an effect of compressing the smoke.

Preferably, a power supply start button 1 and a switch control board 4 are contained in the right cylindrical cavity 22 of the piston support 2, and are configured to be contactable mutually by contact points; the power supply start button 1 is configured to control the energization of the heating element 6.

Preferably, the heating element 6 is spiral.

A second aspect of the present invention relates to a press puffing device including the following components:

a piston support 2 including a left cylindrical cavity 21, a right cylindrical cavity 22, and a connection portion 23 between the left cylindrical cavity and the right cylindrical cavity, wherein both upper and lower ends of the left cylindrical cavity 21 and the right cylindrical cavity 22 are open;

a nozzle holder 12, including a cylindrical inner cavity 123 with a roof, wherein a lateral gas channel 124 is provided on a side wall of the inner cavity 123; the lateral gas channel 124 is connected to an air outlet 121 for air to pass through; and a nozzle holder guide slot 122 penetrating the side wall of the cylindrical inner cavity 123 is provided thereon; and a sealing fixer 14 including a left cavity 141, a right cavity 142 and a partition wall 143 between the left cavity and the right cavity, wherein a sealing fixer sliding slot 144 is provided on the partition wall 143; and an inner shape of the left cavity 141 is matched with an outer shape of the nozzle holder 12;

wherein, positional relationships of various components are as follows:

the nozzle holder 12 is contained in the left cavity 141 of the sealing fixer 14; the right cylindrical cavity 22 of the piston support 2 is contained in the right cavity 142; the sealing fixer sliding slot 144 and the nozzle holder guide slot 122 are configured to overlap each other; the connection portion 23 of the piston support 2 is allowed to pass through and slide upwards and downwards in the sealing fixer sliding slot 144 and the nozzle holder guide slot 122; the left cylindrical cavity 21 of the piston support 2 is contained in the cylindrical inner cavity 123 of the nozzle holder 12; a top end of the left cylindrical cavity 21 can be appressed or not appressed with the roof of the cylindrical inner cavity 123; the lateral gas channel 124 is closed when the top end of the left cylindrical cavity 21 is appressed with the roof, and the lateral gas channel 124 is opened when top end of the left cylindrical cavity 21 is not appressed with the roof.

Advantages of the Present Invention

1. The complicated airflow channel design of the smoking paraphernalia for traditional electrically heated cigarette is omitted, which reduces the processing cost of the equipment. In the smoking paraphernalia for traditional electrically heated cigarette; the air enters the cigarette heating tube along the airflow channel in the smoking paraphernalia and takes out the smoke generated by heating the cigarette, so that the user can smoke. However, the complete design of airflow channel is required to design air inlet holes connected to each other for air to pass through between a plurality of components adjacent to each other, which increases the difficulty of manufacturing components. In the present patent, the cigarette heating tube is ventilated in a one-way direction, and the air fails to enter the heating chamber from the bottom or the side of the heating chamber, the smoke formed in the heating chamber is spurted under the pressure of the piston support due to the increase in pressure, which omits the airflow channel design and decreases the manufacturing difficulty.

2. The heating element works under a radiant heating mode instead of directly contacting the cigarette, leading to uniform heating, and avoiding local overheating.

3. Since the smoke is spurted out under the compression action from the smoking paraphernalia for snorting by the user, without the necessity of using mouth, the cigarette filter is not required, thereby naturally avoiding the contact between the mouth and the cigarette filter, which is convenient and hygienic, and can reduce the direct damage of nicotine in the smoke to the human oral mucosa.

BRIEF DESCRIPTION OF THE DRAWINGS

Wherein FIGS. 6, 8 and 10 are also structural schematic diagrams of a press puffing device of the present invention.

The reference signs are illustrated as follows:

1: power supply start button; 2: piston support; 3: spring; 4: switch control board; 5: cigarette; 6: heating element; 7: thermal insulation pipe; 8: main control circuit board; 9: USB charging port; 10: battery; 11: base; 12: nozzle holder; 13: sealing ring; 14: sealing fixer; 15: cigarette heating tube; 16: roasting-type heating device housing; 17: porous thermal insulation material; 18: housing;

21: left cylindrical cavity; 22: right cylindrical cavity; 23: connection portion; 24: radial inner edge;

121: air outlet; 122: nozzle holder guide slot; 123: cylindrical inner cavity; 124: lateral gas channel; 141: left cavity; 142: right cavity; 143: partition wall; 144: sealing fixer sliding slot; 151: wall hole.

DETAILED DESCRIPTION OF THE EMBODIMENTS

Figure 1:
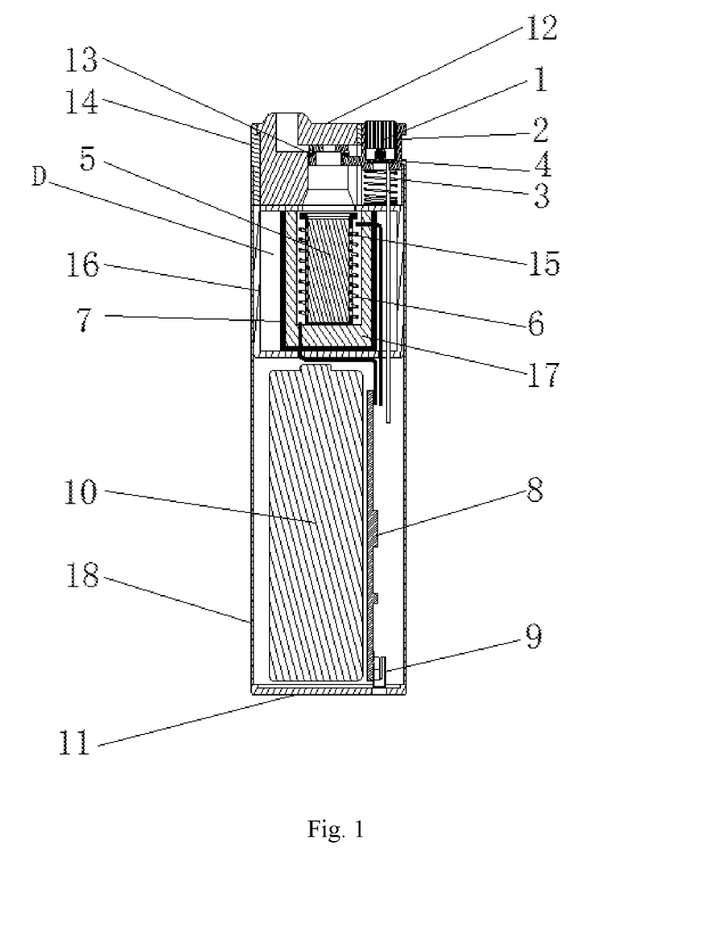
FIG. 1 is a structural schematic diagram showing a press and snorting type smoking paraphernalia for heating a cigarette of the present invention.
Figure 2:
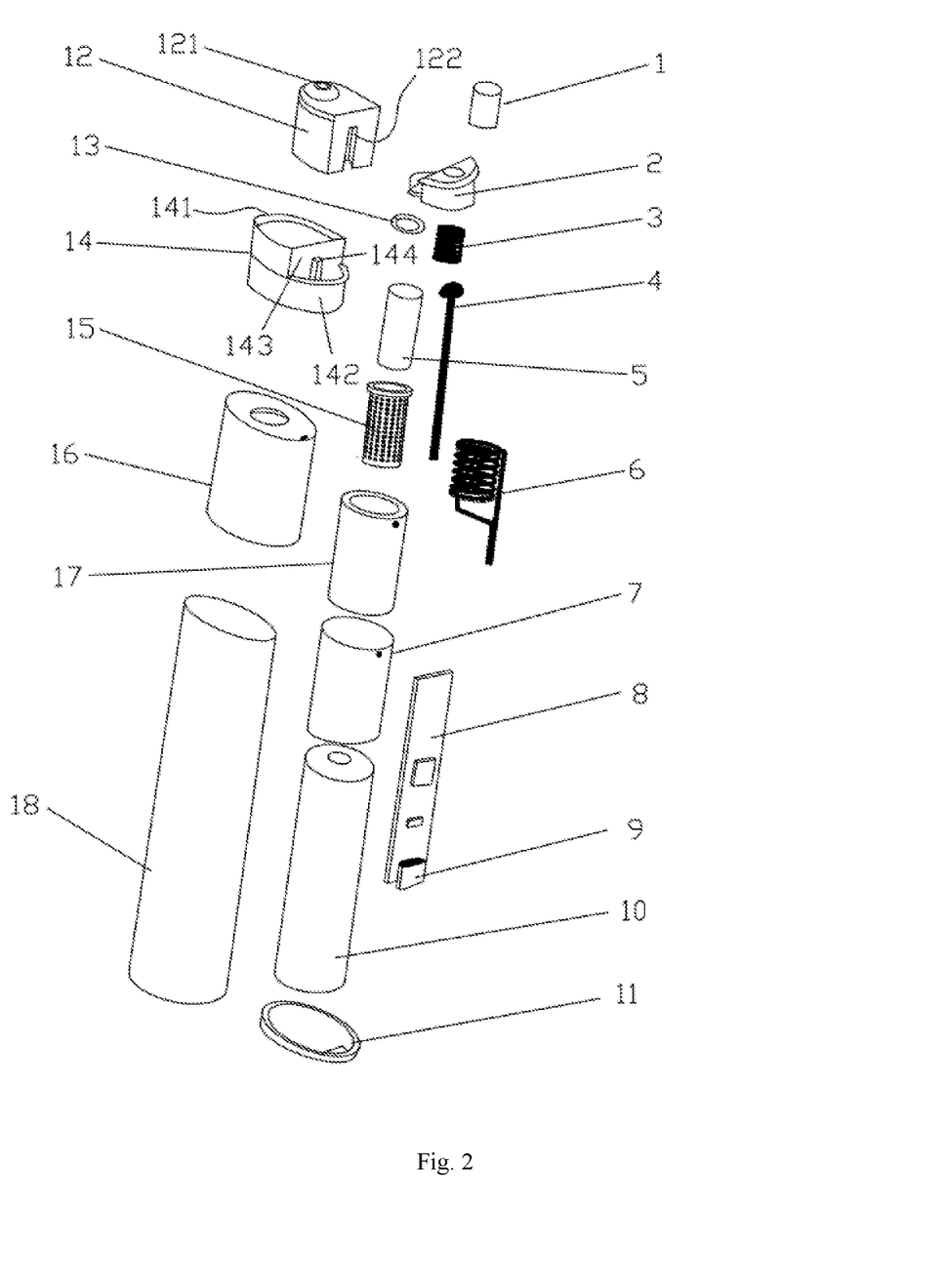
FIG. 2 is an exploded view showing various components of a press and snorting type smoking paraphernalia for heating a cigarette of the present invention.
Figure 3:
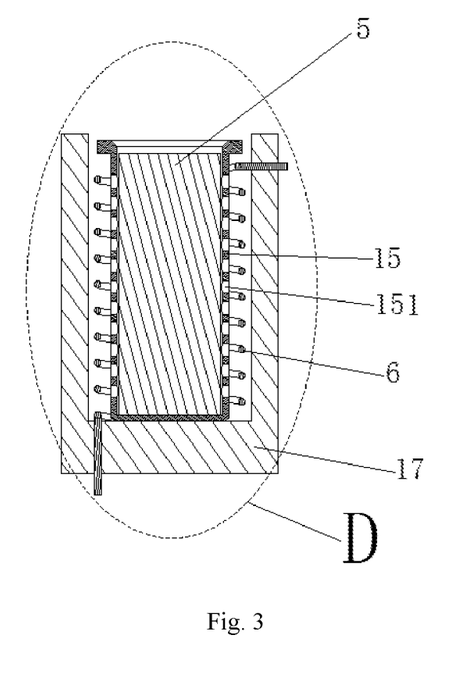
FIG. 3 is a structural schematic diagram showing a roasting-type heating device (namely, portion D in FIG. 1) of a press and snorting type smoking paraphernalia for heating a cigarette of the present invention.
Figure 4:
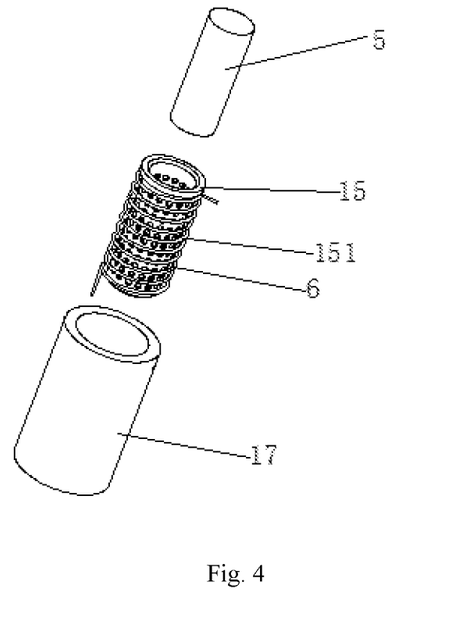
FIG. 4 is an exploded view showing a roasting-type heating device of a press and snorting type smoking paraphernalia for heating a cigarette of the present invention.
Figure 5:
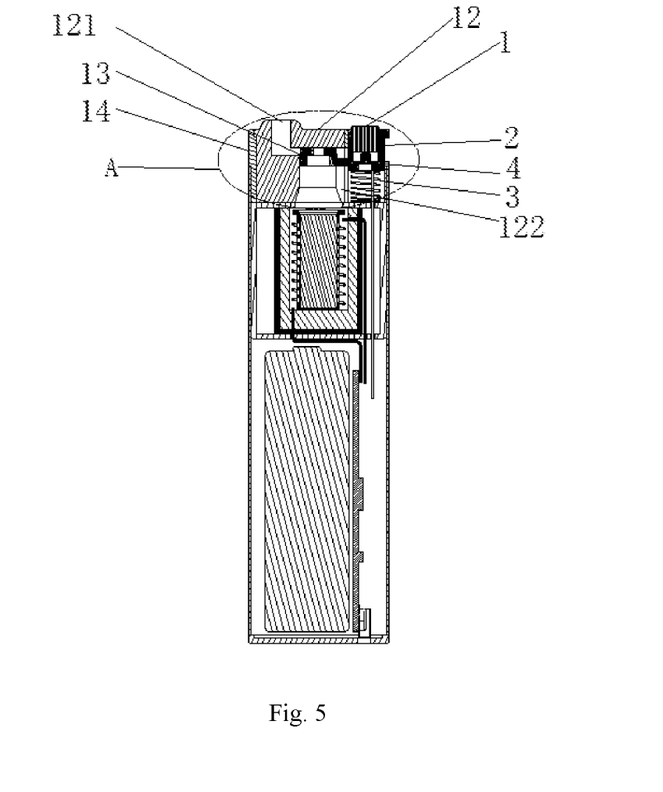
FIG. 5 is a cross-sectional view showing a structure of a press and snorting type smoking paraphernalia for heating a cigarette of the present invention in a non-working state.
Figure 6:
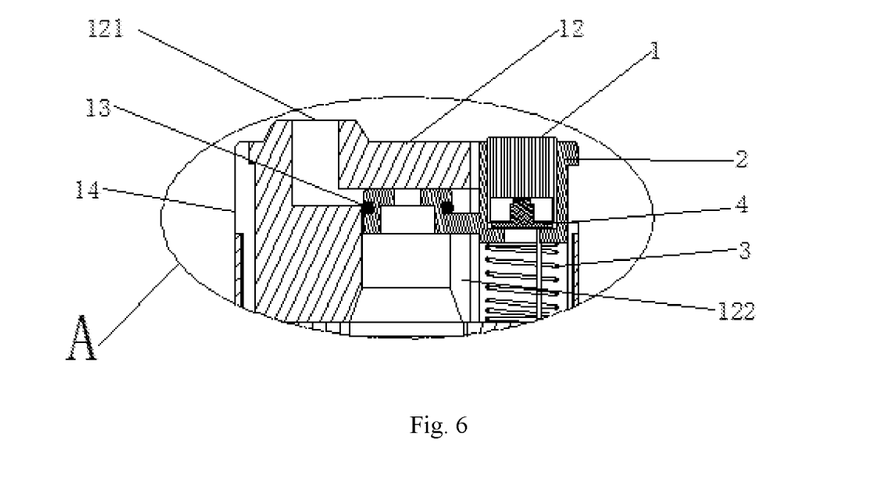
FIG. 6 is an enlarged view showing a portion indicated by a circle A in FIG. 5.
Figure 7:
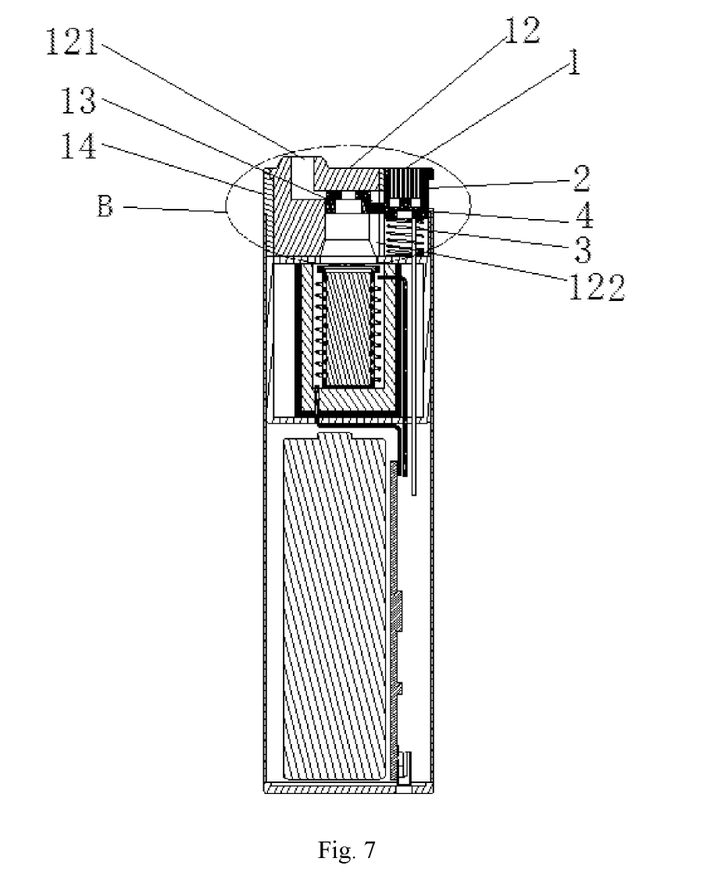
FIG. 7 is a cross-sectional view showing a structure of a press and snorting type smoking paraphernalia for heating a cigarette of the present invention when the power supply start button 1 is pressed and the piston support 2 is not pressed.
Figure 8:
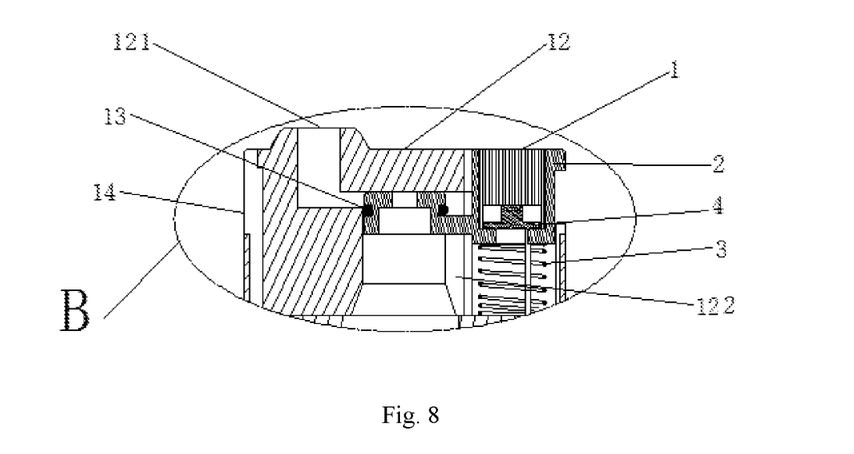
FIG. 8 is an enlarged view showing a portion indicated by a circle B in FIG. 7.
Figure 9:
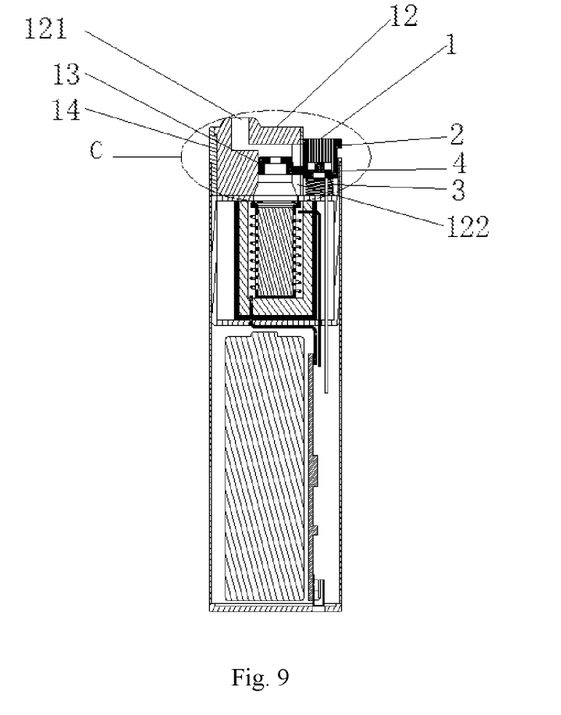
FIG. 9 is a cross-sectional view showing a structure of a press and snorting type smoking paraphernalia for heating a cigarette of the present invention when the piston support 2 is pressed.
Figure 10:
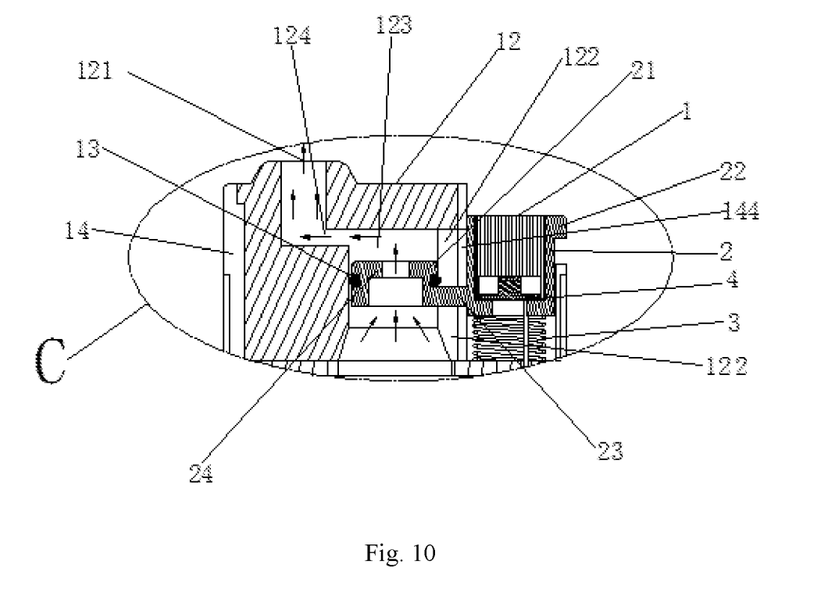
FIG. 10 is an enlarged view showing a portion indicated by a circle C in FIG. 9.

The overall structure of the press and snorting type smoking paraphernalia for heating the cigarette of the present invention is described in the Summary, and the related components and structures thereof can be clearly shown in FIGS. 1-4, which will not be described repeatedly hereinafter.

The working process of the press and snorting type smoking paraphernalia for heating the cigarette of the present invention will be described hereinafter with reference to the drawings:

A solid tobacco material which can be heated by roasting and subjected to a pyrolysis to produce an aroma material is used in the smoking paraphernalia. The solid tobacco material is specially formulated and processed into a cylindrical cigarette. The cigarette 5 is placed in the cigarette heating tube 15.

When the user presses the power supply start button 1 and does not press the piston support 2, the heating element 6 suspended between the cigarette heating tube 15 and the thermal insulation pipe 7 is energized to start generating heat. The heat generated by the heating element is transmitted to the surface of the cigarette 5 through the wall hole 151 on the cigarette heating tube 15 in the radiated manner, and gradually penetrates into the center of the cigarette 5. Meanwhile, the cigarette heating tube also receives the radiation heat from the heating element to be heated, and conductively heats the cigarette contained in the cigarette heating tube. The tobacco material volatilizes the aroma gas after being heated. The aroma gas is contained in the cylindrical inner cavity 123.

Since the user has not pressed the piston support 2 at this time, the top end of the left cylindrical cavity 21 is appressed with the roof of the cylindrical inner cavity 123, and the side wall of the left cylindrical cavity 21 closes the lateral gas channel 124. In this way, the cylindrical inner cavity 123 is in a sealed state, so that the aroma gas remains inside the cylindrical inner cavity.

When the user presses the piston support 2 downwards, the left cylindrical cavity 21 moves downwards accordingly, so that the top end of the left cylindrical cavity is not appressed with the roof of the cylindrical inner cavity 123. In this way, the side wall of the left cylindrical cavity 21 does not block the lateral gas channel 124, thereby the lateral gas channel 124 is opened. Meanwhile, the volume of the cylindrical inner cavity 123 is reduced, so that the smoke contained in the cylindrical inner cavity is compressed and flows to the air outlet 121 through the lateral gas channel 124, and then is spurted out for snorting by the user. The spring 3 is also compressed while the user presses the piston support 2 downwards.

When the user releases the piston support 2, the piston support 2 returns to the original position under the resilience of the spring 3.

When the user wants to smoke next time, repeat the above-mentioned processes.

What is claimed is:
1. A press puffing device, comprising:
   a piston support, comprising a left cylindrical cavity, a right cylindrical cavity, and a connection portion between the left cylindrical cavity and the right cylindrical cavity, wherein an upper end and a lower end of the left cylindrical cavity and an upper end and a lower end of the right cylindrical cavity are open;
   a nozzle holder, comprising a cylindrical inner cavity with a roof, wherein a lateral gas channel is provided on a side wall of the cylindrical inner cavity; the lateral gas channel is connected to an air outlet for air to pass through; and a nozzle holder guide slot penetrating the side wall of the cylindrical inner cavity is provided on the side wall of the cylindrical inner cavity;
   a sealing fixer, comprising a left cavity, a right cavity and a partition wall between the left cavity and the right cavity, wherein a sealing fixer sliding slot is provided on the partition wall; and an inner shape of the left cavity is matched with an outer shape of the nozzle holder; and
   a roasting-type heating device, comprising a cigarette heating tube, a heating element, and a thermal insulation pipe, wherein the heating element is disposed on an outer side of the cigarette heating tube; the thermal insulation pipe is sleeved on an outer side of the heating element; a porous thermal insulation material is disposed between the heating element and the thermal insulation pipe; and a shape of the porous thermal insulation material is cylindrical; and wherein a solid tobacco material is heated by roasting and subjected to a pyrolysis to produce an aroma material, and the solid tobacco material is formulated and processed into a cylindrical cigarette, and the cigarette is placed in the cigarette heating tube;
   wherein, the nozzle holder is contained in the left cavity of the sealing fixer; the right cylindrical cavity of the piston support is contained in the right cavity; the sealing fixer sliding slot and the nozzle holder guide slot are configured to overlap each other; the connection portion of the piston support is allowed to pass through and slide upwards and downwards in the sealing fixer sliding slot and the nozzle holder guide slot; the left cylindrical cavity of the piston support is contained in the cylindrical inner cavity of the nozzle holder; a top end of the left cylindrical cavity is appressed or not appressed with the roof of the cylindrical inner cavity; the lateral gas channel is closed when the top end of the left cylindrical cavity is appressed with the roof, and the lateral gas channel is opened when the top end of the left cylindrical cavity is not appressed with the roof.

2. The press puffing device according to claim 1, wherein a sealing ring is sleeved between the left cylindrical cavity of the piston support and the cylindrical inner cavity of the nozzle holder.

3. The press puffing device according to claim 1, wherein a spring is contained in the right cavity of the sealing fixer; a first end of the spring abuts against a lower end wall of the right cylindrical cavity of the piston support; and a second end of the spring abuts against a bottom wall of the sealing fixer.

4. The press puffing device according to claim 1, wherein a radial inner edge is provided in a top opening of the left cylindrical cavity of the piston support.

* * * * *